United States Patent [19]

Hobo

[11] 4,261,696
[45] Apr. 14, 1981

[54] DENTAL FACEBOW

[75] Inventor: Sumiya Hobo, Tokyo, Japan

[73] Assignee: Denar Corporation, Anaheim, Calif.

[21] Appl. No.: 19,737

[22] Filed: Mar. 12, 1979

[30] Foreign Application Priority Data

Mar. 17, 1978 [JP] Japan .................................. 53-034121

[51] Int. Cl.³ ............................................. A61C 19/04
[52] U.S. Cl. ...................................................... 433/73
[58] Field of Search .......................................... 433/73

[56] References Cited

U.S. PATENT DOCUMENTS

| 1,052,806 | 2/1913 | Evans | 433/73 |
|---|---|---|---|
| 2,334,643 | 11/1943 | Moore | 433/73 |
| 2,814,876 | 12/1957 | Stuart | 433/73 |
| 3,052,030 | 9/1962 | Spence | 433/73 |
| 3,130,494 | 4/1964 | MacKay | 433/73 |
| 3,206,852 | 9/1965 | Swanson | 433/56 |
| 3,218,716 | 11/1965 | Stuart | 433/73 |
| 3,350,782 | 11/1967 | Guichet | 433/73 |
| 3,431,649 | 3/1969 | Guichet | 433/73 |
| 3,464,115 | 9/1969 | Baker | 433/73 |
| 3,490,146 | 1/1970 | Guichet | 433/73 |

OTHER PUBLICATIONS

"Practical Analysis of Occlusal Procedures" in J. Pros. Den. May–Jun. 1966 pp. 557–571.

Primary Examiner—Robert Peshock
Attorney, Agent, or Firm—Edward D. O'Brian

[57] ABSTRACT

A facebow for use in measuring the positions of the temporomandibular joints of a patient relative to the maxillary teeth of the patient so that such positions may be transferred to an articulator may be constructed so as to utilize two normally spaced side arms which are connected by a mechanical structure permitting the arms to be moved linearly toward and away from one another. A mechanical structure is provided for accomplishing such movement in such a manner that when either of the arms is moved the other arm is concurrently moved in a corresponding manner. The connecting structure carries a frame including a bite fork or equivalent adapted to be positioned in the mouth of a patient along or adjacent to the maxillary teeth in making an impression of these teeth. The frame carrying the bite fork is capable of being adjusted relative to the connecting structure and thus relative to the arms.

11 Claims, 3 Drawing Figures

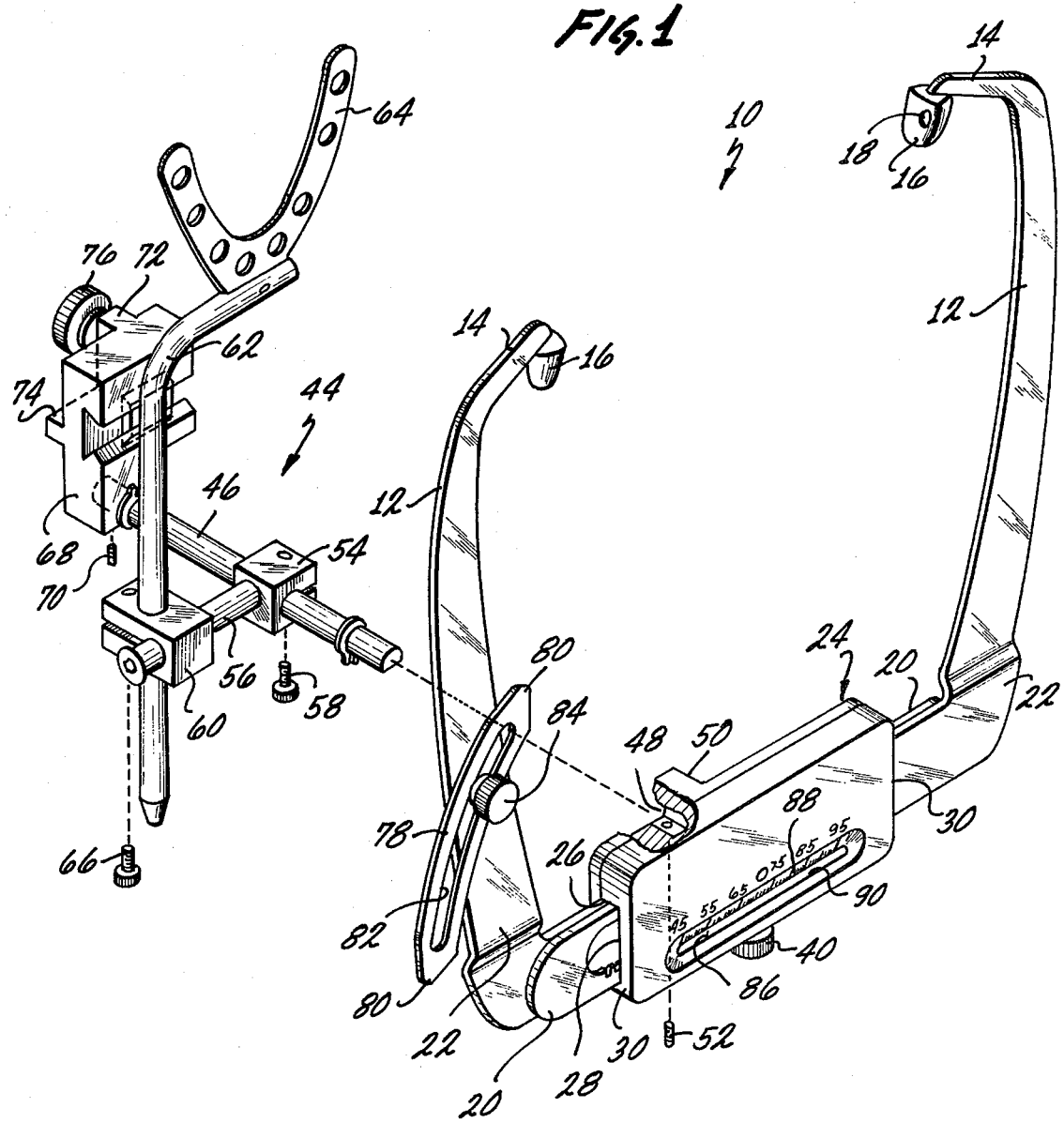

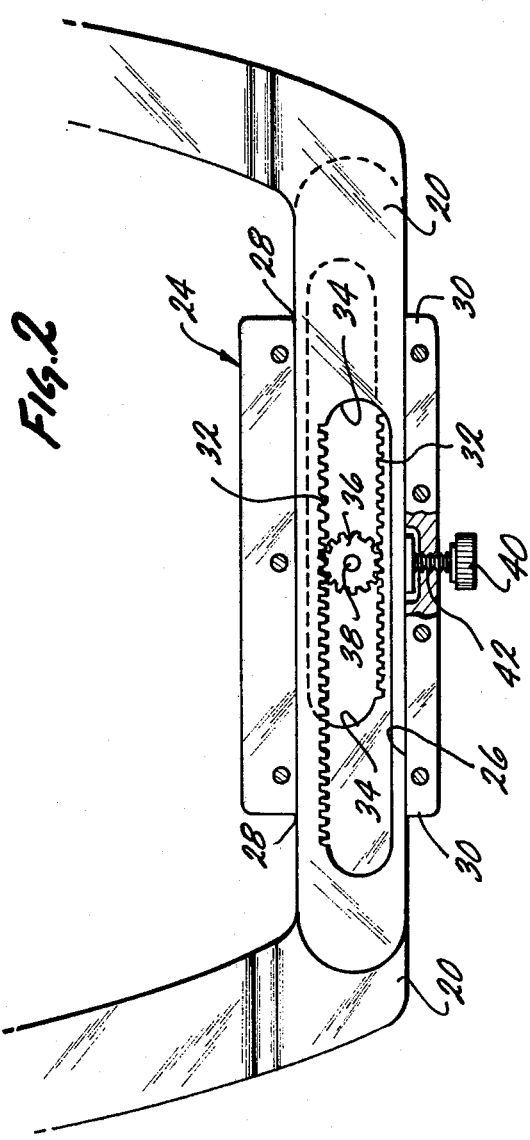
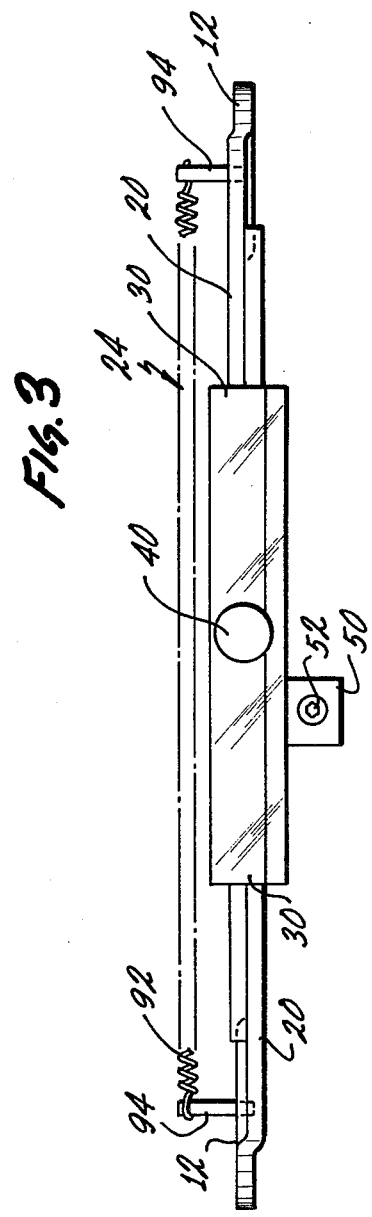

DENTAL FACEBOW

BACKGROUND OF THE INVENTION

The invention set forth in this specification pertains to new and improved dental facebows.

It is well established that dental facebows are utilized in measuring or determining the positions of the temporomandibular joints of a patient relative to the patient's maxillary teeth so that such relative positions may be transferred to a dental articulator. Such measurements are useful in the operation of the articulator for a variety of dental purposes. It is not considered that an understanding of the present invention requires any detailed explanation as to the reasons why such relative measurements are made and the reasons why such measurements are transferred to the articulator. These items are considered to be well established in the dental field.

It is, however, considered necessary to understand that prior dental facebows have been constructed so as to include side arms connected by a mechanical connecting structure. As used these side arms are located at the sides of the head of a patient while the connecting structure is located generally in front of the face of the patient. These prior facebows have normally been constructed so as to include a frame or frame-type structure including a so-called dental fork or an equivalent member mounted on the connecting structure so that the dental fork can be inserted within the patient's mouth against or adjacent to the maxillary teeth in making an impression of the patient's maxillary teeth. During the use of the facebow the dental fork holds such an impression.

Such prior facebows have been constructed in a number of different ways. Many such prior units have been constructed so that so-called styli or positioning members located on ends of the arms are separately moved relative to the head of a patient after the arms are secured so as to be immobile with respect to one another and after the dental fork is located in an appropriate position in the mouth. Structures of this type are considered to be relatively difficult to use in obtaining accurate measurements.

It is considered this has led to the development of another type of facebow structure in which two generally C-shaped arms are pivotally connected by a link so that these arms have ends which are adapted to be located on opposite sides of the head of a patient and so that these arms have overlapping ends which may be clamped together. This type of dental facebow normally carries a framework including a dental fork on the connecting link. Structures of this type are considered to be disadvantageous in making accurate measurements which can be transferred to an articulator because of the linkage system employed. The type of linkage used in such dental facebows shifts the position of a dental fork relative to the ends of the arms used for measurement purposes slightly as a result of the pivoting of the arms with respect to the connecting link.

BRIEF SUMMARY OF THE INVENTION

As a result of these considerations it is considered there is a need for new and improved dental facebows. A broad or basic object of the present invention is intended to provide new and improved dental facebows which can be easily and conveniently utilized in measuring or determining the position of the temporomandibular joints of a patient relative to the patient's maxillary teeth so that such relative positions may be easily and conveniently transferred to a dental articulator.

A further objective of the present invention is to provide facebows which are constructed so that the central-most portions of such facebows (which may be referred to as a bow proper) may be utilized with different frames including dental forks or equivalent elements in such a manner that only one such frame together with a reading from the facebow itself need be utilized in transferring measurements to an articulator. Further objectives of the present invention are to provide dental facebows which may be easily and conveniently constructed at a comparatively nominal cost, and which are capable of repeated utilization in making accurate measurement which may be transferred to articulators.

In accordance with this invention these various objectives are achieved by providing a facebow for use in measuring the positions of the temporomandibular joints of a patient relative to the maxillary teeth so that such positions may be transferred to an articulator, the facebow including two, spaced side arms, connecting means connecting to arms to one another so that the arms are supported relative to one another by the connecting means and frame means including a bite fork means located on the connecting means so as to extend therefrom in which the improvement comprises: the connecting means securing the arms to one another so as to permit the arms to be moved linearly toward and away from one another, moving means for simultaneously moving both of the arms toward and away from one another and holding means for preventing movement of the arms.

BRIEF DESCRIPTION OF THE DRAWING

The invention is best more fully described with reference to the accompanying drawing in which:

FIG. 1 is an isometric view of a presently preferred embodiment or form of a facebow in accordance with this invention;

FIG. 2 is a partial cross-sectional view taken at line 2—2 of FIG. 1; and

FIG. 3 is a front elevational view of a slightly modified form of a facebow as illustrated in FIG. 1 without the jig frame illustrated in FIG. 1 attached which differs from the facebow illustrated in FIG. 1 only as to the inclusion of a spring and mountings.

The concepts or principles of this invention embodied within the particular facebow illustrated in the drawing are set forth and defined in the appended claims forming a part of this specification. It is considered that these concepts or principles may be easily utilized in other facebows which differ from the precise facebow illustrated as to matters of routine mechanical skill. For this reason this invention is not to be considered as being limited to facebows which are constructed in the precise manner illustrated.

DETAILED DESCRIPTION

The facebow 10 illustrated in FIGS. 1 and 2 of the drawing is constructed so as to utilize two slightly curved, substantially parallel flat arms 12 which are adapted to be located along the sides of the head of a patient during the use of this facebow 10. The arms 12 are provided with ends 14 which extend toward one another. Preferably these ends 14 are provided with enlarged extremities 16 which are adapted to engage the head of a patient without discomfort. If desired these extremities 16 may be provided with aligned depressions or holes 18 which may be used for reference purposes in transferring measurements made using the facebow 10 to an articulator.

These extremities 16 may be shaped in many different ways and may be described utilizing various different terms. Thus, for example, corresponding extremities in prior facebows are frequently somewhat pointed in character and have commonly been referred to as styli. It is considered desirable to have these extremities 16 sufficiently rounded so that they will not cause patient discomfort. On the other hand, they must be sufficiently restricted in dimension so as to be capable of being precisely located relative to a patient's head in accordance with conventional practice.

Each of the arms 12 is provided with a flat leg 20. These legs 20 are located at nearly right angles to the arms 12 so that they project toward one another as illustrated in FIG. 1 of the drawing. Preferably these legs 20 are flat so that they can lie against one another and can move adjacent to one another. Small offsets 22 are provided in the arms 12 adjacent to the legs 20 so as to accommodate the legs 20 fitting against one another in this manner as the arms 12 are located in a common flat plane (not shown).

The facebow 10 includes as a connecting means (not separately numbered) an elongated, essentially box-like bearing member 24 including an interior elongated bearing opening 26 of rectilinear cross-section extending between openings 28 at opposed ends 30 of the member 24. The legs 20 are located so as to overlie one another within this bearing opening 26; these legs 20 are also dimensioned so that they fit closely against one another and against the interior (not separately numbered) of the bearing opening 26 in such a manner as to permit or accommodate lineal movement of the arms 12 in a parallel manner toward and away from one another.

In the facebow 10 such movement is achieved by utilizing gear racks 32 located along edges (not separately numbered) of elongated slot-like openings 34 in each of the legs 20. These openings 34 are located generally within the bearing member 24. The gear racks 32 on the two legs 20 are coupled mechanically so as to cause simultaneous movement of the arms 12 and 14 either toward or away from one another through the use of a small spur gear 36 located within the opening 26 and within the openings 34 so as to couple with both of the gear racks 32. This gear 36 is preferably rotatably mounted on a small shaft 38 mounted on the bearing member 26 so as to extend through the bearing member 24. A small conventional locking screw 40 may be threaded within an opening 42 in the bearing member 24 for the purpose of securing both of the legs 20 and of course, hence, the arms 12 against relative movement.

The bearing member 24 is used to hold what may be regarded as a jig, frame of framework 44. This jig 44 includes a downwardly extending rod 46 which is normally mounted within a hole 48 and a mounting block 50 forming a part of the bearing member 24. A conventional set screw 52 is preferably used to secure the rod 46 in place. A small clamp block 54 which is rigidly secured to a cross rod 56 is preferably mounted on the rod 46 through the use of another set screw 58 in such a manner that its position along the rod 46 may be linearly adjusted as desired. Another clamp block 60 is secured on the cross rod 56 for the purpose of holding an elongated support rod 62 of an L-shaped character. This support rod 62 carries a so-called dental fork 63 useful in making or holding an impression during the use of the facebow 10. The clamp block 60 is constructed as shown so that a single set screw 66 may be used to rigidly position the support rod 62 with respect to the cross rod 56.

The extremity (not separately numbered) of the rod 46 remote from the bearing member 24 carries a small mounting block 68 which is primarily useful in mounting the frame or jig 44 upon the base of an articulator. This mounting block 68 is secured in place by means of another set screw 70. It is preferably equipped with a bottom wall 72 which is adapted to slide within a groove (not shown) in an articulator and a stop wall 74 which is adapted to abut against a portion of the articulator in mounting the jig or frame 44 on the articulator. A small screw clamp 76 may be located on the mounting block 68 for the purpose of securing it in place on an articulator.

The facebow 10 is preferably also constructed so as to utilize an orbital pointer 78 for use in establishing an individual's horizontal plane during the use of this facebow 10. This pointer 78 is preferably an elongated, somewhat curved bar having slightly rounded ends 80 which are not apt to cause patient discomfort. This pointer carries an elongated slot 82 enabling it to be clamped in any of a variety of positions relative to one of the arms 12 through the use of a thumb screw 84. If desired, other conventional means for orienting the facebow 10 relative to the head of a patient may be mounted in the same or in other locations on the facebow 10.

The particular facebow 10 is considered to be quite desirable inasmuch as it is constructed so that the distance between the extremities 16 can be determined by taking a reading of the position of a marker 86 on one of on one of the legs 20 relative to a scale 88 located on the bearing member 26 immediately adjacent to an elongated opening 90 in this member 24. This particular structure is considered to be a rather simple structure for its intended purpose. If desired, various other equivalent measuring means such as, for example, dial indicators may be utilized in indicating the relative positions of the extremeties 16. Corresponding readings can be obtained by appropriate markings made on both of the legs 20.

Inasmuch as the use of facebows corresponding to the facebow 10 is well established in the dental field it it not considered necessary to describe the use of this facebow 10 in detail in this specification. Essentially it is utilized in a conventional manner. The facebow 10 is, however, considered to be much more desirable than prior facebows for several reasons. One of these pertains to the ease with which the arms 12 may be adjusted relative to one another so as to obtain a reading visible at the scale 88 indicating their relative positions. Another important factor is considered to be the fact that the arms 12 can only be moved simultaneously in the same parallel orientation toward and away from one another. This is important in establishing what may be referred to as a rectilinear coordinate system with reference to the frame or jig 44 enabling measurements to be accurately transferred to an articulator.

Because of the construction of the facebow 10 different frames or jigs 44 may be utilized with the remainder of this structure. Thus, for example, in a dental office in order to transfer measurements from a number of patients to various different articulators as time permits it is only necessary to utilize different frames or jigs 44 and to record the measurements between the extremeties 16 taken with each of such jigs or frames 44.

If for any reason, such as wear or manufacturing tolerances, backlash should tend to interfere with the accuracy of measurements obtained using the facebow 10, it is possible to utilize various known mechanical expedients in controlling the effects of such backlash. Thus, for example, as indicated in FIG. 3 a small coil spring 92 may be mounted on brackets 94 which in turn are located on the legs 20 for the purpose of biasing the arms 12 toward one another. When a spring such as the spring 92 is used it is preferable to have it located parallel to the bearing opening 26 and as close to this bearing opening 26 as reasonably possible in order to minimize cocking since such cocking might tend to interfere with the desired parallel movement of the arms 12 toward and away from one another.

Similarly, a number of other changes may be made in the facebow 10 so as to achieve essentially lineal type movement of the arms 12 toward and away from one another. Since various parallel movement structures are well known in the mechanical linkage field it is not considered to describe alternative structures in this specification or to illustrate them in the drawing. The particular structure of the facebow 10 described is considered to be preferable over all such other structures because of its simplicity and effectiveness.

I claim:

1. A facebow for use in measuring the positions of the temporomandibular joints of a patient relative to the maxillary teeth so that such positions may be transferred to an articulator, said facebow including two spaced side arms, connecting means connecting said arms to one another so that said arms are supported relative to one another by said connecting means, and frame means including means for holding an impression of the maxillary teeth located on said connecting means so as to extend therefrom in which the improvement comprises:
   said arms include legs which extend generally toward one another,
   said connecting means for holding said arms to one another so as to permit said arms to be moved linearly toward and away from one another, and
   said connecting means comprise parallel lineal bearing means for supporting said legs adjacent to one another so that said arms can only be moved linearly toward and away from one another so that said arms remain parallel to one another at all times,
   moving means for simultaneously moving both of said arms toward and away from one another, located on said connecting means,
   said moving means extending between and contacting both of said legs and being capable of being manually operated so as to vary the spacing between said arms by moving said legs within said bearing means,
   separate holding means for preventing movement of said arms located on said connecting means.

2. A facebow as claimed in claim 1 including:
   scale means for indicating the relative spacing between said arms.

3. A facebow for use in measuring the positions of the temporomandibular joints of a patient relative to the maxillary teeth so that such positions may be transferred to an articulator, said facebow including two spaced side arms, connecting means connecting said arms to one another so that said arms are supported relative to one another by said connecting means, and frame means including means for holding an impression of the maxillary teeth located on said connecting means so as to extend therefrom in which the improvement comprises:
   said connecting means securing said arms to one another so as to permit said arms to be moved linearly toward and away from one another,
   moving means for simultaneously moving both of said arms toward and away from one another,
   said arms include legs which extend generally toward one another, and
   said connecting means comprise lineal bearing means for supporting said legs so that said arms can only be moved toward and away from one another,
   said moving means includes two gear racks, one of said racks being located on one of said legs and the other of said racks being located on the other of said legs, and a spur gear located generally between said gear racks in engagement with said gear racks, said spur gear transmitting lineal movement of one of said arms to the other of said arms during the utilization of said facebow.

4. A facebow as claimed in claim 3 wherein:
   said spur gear is rotatably mounted on said connecting means.

5. A facebow as claimed in claim 3 including:
   anti-backlash means for preventing play between said racks and said spur gear.

6. A facebow for use in measuring the positions of the temporomandibular joints of a patient relative to the maxillary teeth so that such positions may be transferred to an articulator, said facebow including two spaced side arms, connecting means connecting said arms to one another so that said arms are supported relative to one another by said connecting means, and frame means including means for holding an impression of the maxillary teeth located on said connecting means so as to extend therefrom in which the improvement comprises:
   said connecting means securing said arms to one another so as to permit said arms to be moved linearly toward and away from one another, and
   moving means for simultaneously moving both of said arms toward and away from one another,
   said connecting means comprises an elongated bearing member having an elongated bearing opening located therein, said bearing opening having opposed open ends,
   each of said arms includes a leg, said legs and said arms extending into said bearing opening from opposite ends thereof, said legs overlapping one another within said bearing opening,
   said moving means including two gear racks, one of said gear racks being located on one of said legs and the other of said gear racks being located on the other of said legs, said gear racks being located so as to extend parallel from one another and so as to be spaced from one another, said gear racks being positioned on said legs so as to be opposite one another within the interior of said bearing opening,
   said moving means also including a spur gear rotatably mounted on said bearing member within the interior of said bearing opening, said spur gear being located between said gear racks and mating with both of said gear racks.

7. A facebow as claimed in claim 6 including:
   scale means for indicating the relative spacing between said arms, and holding means for preventing movement of said arms.

8. A facebow as claimed in claim 6 including:
an elongated opening within said bearing member, a part of one of said legs being visible through said opening in all positions of said arms,
a marker on said one of said legs, and
a scale indicating the relative spacing between said arms located on said bearing member adjacent to said opening and said marker so that the relative positions of said arms may be determined by the position of said marker relative to said scale.

9. A facebow as claimed in claim 6 wherein:
said holding means comprises a clamping screw mounted on said bearing member and capable of being brought into engagement with both of said legs to prevent movement of said arms.

10. A facebow as claimed in claim 6 including:
spring means connecting said arms so as to bias said arms toward one another.

11. A facebow as claimed in claim 6 including:
an elongated opening within said bearing member, a part of one of said legs being visible through said opening in all positions of said arms,
holding means for preventing movement of said arms,
a marker on said one of said legs,
a scale indicating the relative spacing between said arms located on said bearing member adjacent to said opening and said marker so that the relative positions of said arms may be determined by the position of said marker relative to said scale, and
spring means connecting said arms so as to bias said arms toward one another, and wherein
said holding means comprises a clamping screw mounted on said bearing member and capable of being brought into engagement with both of said legs to prevent movement of said arms.

* * * * *